(12) United States Patent
Hogan

(10) Patent No.: US 8,570,528 B2
(45) Date of Patent: Oct. 29, 2013

(54) DUAL WAVELENGTH SCANNING SYSTEM

(76) Inventor: Josh N. Hogan, Los Altos, CA (US)

( * ) Notice: Subject to any disclaimer, the term of this patent is extended or adjusted under 35 U.S.C. 154(b) by 0 days.

(21) Appl. No.: 13/429,346

(22) Filed: Mar. 24, 2012

(65) Prior Publication Data

US 2012/0245440 A1 Sep. 27, 2012

Related U.S. Application Data

(60) Provisional application No. 61/465,797, filed on Mar. 24, 2011.

(51) Int. Cl.
*G01B 9/02* (2006.01)

(52) U.S. Cl.
USPC .......................................................... 356/479

(58) Field of Classification Search
USPC ................................................ 356/479, 497
See application file for complete search history.

(56) References Cited

U.S. PATENT DOCUMENTS 6,198,540 B1 * 3/2001 Ueda et al. ..................... 356/479
6,728,571 B1 * 4/2004 Barbato ......................... 600/478

* cited by examiner

*Primary Examiner* — Tarifur Chowdhury
*Assistant Examiner* — Jonathon Cook

(57) ABSTRACT

The invention provides high speed, low cost scanning suitable for time domain OCT systems. According to the preferred embodiment, the apparatus includes a piezo scanning device and partial reflecting surfaces that simultaneously generate two sets of multiple reference signals at two different wavelengths that can span different regions of a target enabling acquiring target information from a large range within the target. In one embodiment of the invention, information from both the front region and the back region of an eye is acquired in a coordinated manner.

15 Claims, 5 Drawing Sheets

DUAL WAVELENGTH SCANNING SYSTEM

CROSS REFERENCES TO RELATED PATENTS OR APPLICATIONS

This utility application, is related to and claims priority from U.S. provisional patent application, 61/465,797, file date Mar. 24, 2011. The subject matter of this application is related to U.S. Pat. No. 7,526,329 entitled Multiple Reference Non-invasive Analysis System and U.S. Pat. No. 7,751,862 entitled Frequency Resolved Imaging System.

FIELD OF THE INVENTION

The invention described and illustrated in this application relates to non-invasive imaging and analysis techniques such as Optical Coherence Tomography (OCT). In particular it relates scanning mechanisms suitable for time domain OCT systems.

This invention also relates to the use of such OCT systems for non-invasive imaging and analysis of targets and non-invasive analysis of concentrations of specific components or analytes in a target, such as the concentration of glucose in blood, tissue fluids, tissue, or components of an eye or other biological entities. This invention also relates to analysis or monitoring for manufacturing defects in components for improved quality control.

BACKGROUND OF THE INVENTION

Non-invasive analysis of targets is a valuable technique for acquiring information about systems or targets without undesirable side effects, such as damaging the target or system being analyzed. In the case of analyzing living entities, such as human tissue, undesirable side effects of invasive analysis include the risk of infection along with pain and discomfort associated with the invasive process. In the case of quality control, it enables non-destructive imaging and analysis on a routine basis, for example, for quality control purposes.

Optical coherence tomography (OCT), is a technology for non-invasive imaging and analysis. OCT typically uses a broadband optical source, such as a super-luminescent diode (SLD), to probe and analyze or image a target. It does so by applying probe radiation from the optical source to the target and interferometrically combining back-scattered probe radiation from the target with reference radiation also derived from the optical source.

The typical OCT optical output beam has a broad bandwidth and short coherence length. The OCT technique involves splitting the output beam into probe and reference beams, typically by means of a beam-splitter, such as a pellicle, a beam-splitter cube or a fiber coupler. The probe beam is applied to the system to be analyzed (the target). Light or radiation is scattered by the target, some of which is back-scattered to form a back-scattered probe beam, herein referred to as signal radiation.

The reference beam is typically reflected back to the beam-splitter by a mirror. Light scattered back from the target is combined with the reference beam, also referred to as reference radiation, by the beam-splitter to form co-propagating reference radiation and signal radiation. Because of the short coherence length only light that is scattered from a depth within the target whose optical path length is substantially equal to the path length to the reference mirror can generate a meaningful interferometric signal.

Thus the interferometric signal provides a measurement of scattering properties at a particular depth within the target. In a conventional time domain OCT system, a measurement of the scattering values at various depths can be determined by varying the magnitude of the reference path length, typically by moving the reference mirror. In this manner the scattering value as a function of depth can be determined, i.e. the target can be scanned.

There are various techniques for varying the magnitude of the reference path length. Because electro-mechanical voice coil actuators can have considerable scanning range, however, there are problems with maintaining the stability or pointing accuracy of the mirror. Fiber based systems use fiber stretchers, however, fiber stretchers have speed limitations and have size and polarization issues. Rotating diffraction gratings can run at higher speeds, however, are alignment sensitive and are too bulky.

Piezo devices can achieve high speed scanning and can have high pointing accuracy, however to achieve a large scanning range requires expensive controls systems and have limited high speed capability.

A scanning method that effectively amplifies the scan range of a piezo device is described in the patents numbered U.S. Pat. Nos. 7,526,329 and 7,751,862. The method taught in these patents uses multiple reference signals with increasing scan range and correspondingly increasing frequency interference signals.

While the multiple reference scanning method can achieve a relatively large scan range at high speed with good pointing stability, there are applications, such as ophthalmic applications, that require imaging or measurements can span significantly larger distances than can be spanned even by amplified piezo scans. In the ophthalmic application, information spanning the full axial length of an eye (of the order of 28 mm) is required.

There is therefore an unmet need for a method, apparatus and system that can achieve large scan range of up to approximately 30 mm at high speed with good pointing stability.

SUMMARY OF THE INVENTION

The invention taught herein meets at least all of the aforementioned unmet needs. The invention provides a method, apparatus and system for high speed, low cost scanning suitable for time domain OCT systems. It includes a piezo scanning device and partial reflecting surfaces that simultaneously generate two sets of multiple reference signals at two different wavelengths that can span different regions of a target enabling acquiring target information from a large range within the target. The invention enables acquiring information from known, predetermined depths in two target regions where such target regions may separated at some distance. The invention therefore, provides for scanning, for example, both the front region and the back region of an eye.

DETAILED DESCRIPTION OF THE INVENTION

Figure 1:
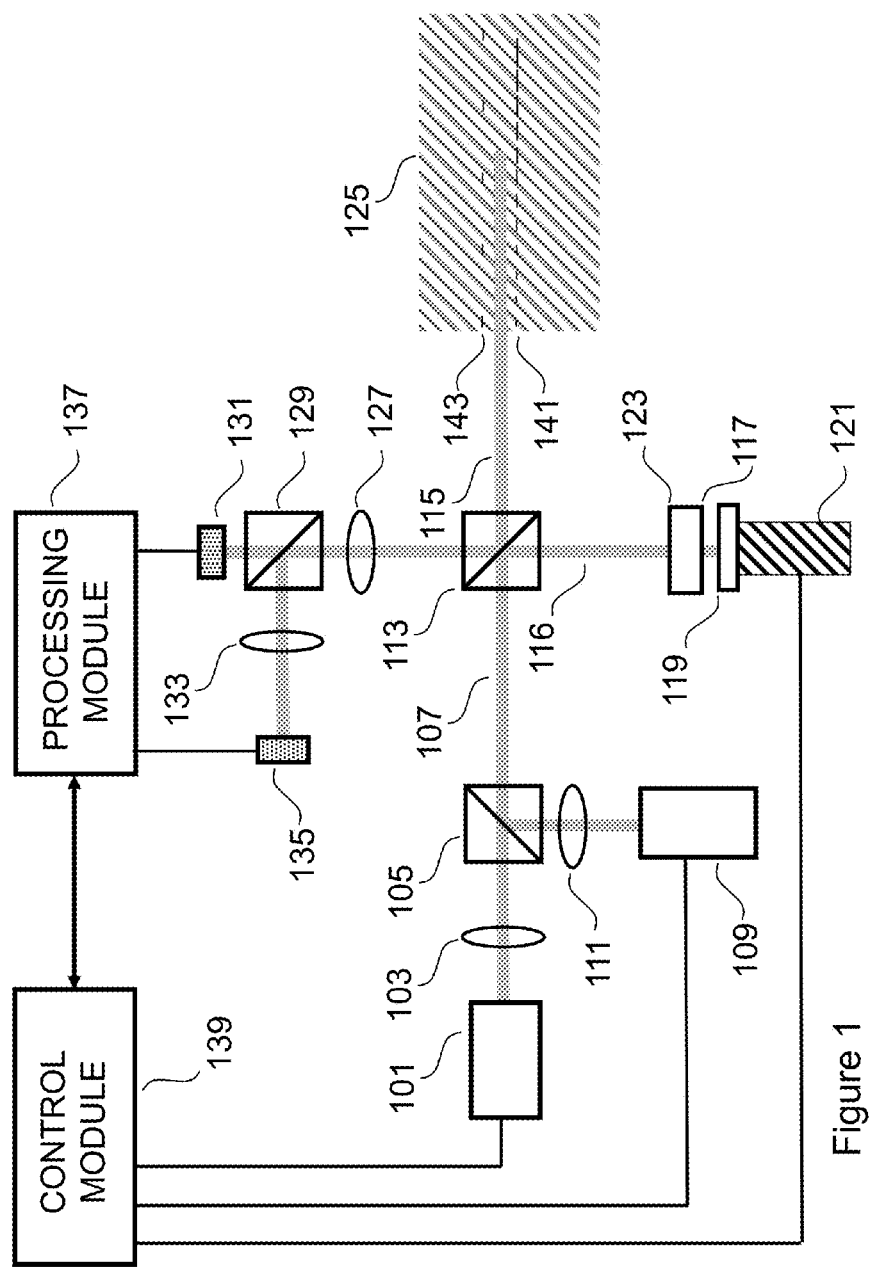
FIG. 1 is a schematic type illustration of a preferred embodiment of the analysis system according to the invention.

The preferred embodiment is illustrated in FIG. 1 illustration where a broadband optical source 101 generates broadband radiation with a wavelength range centered at a first wavelength. The first wavelength radiation is focused by a lens 103, through a beam-splitter 105 that is transmissive (or transparent) for radiation at the first wavelength range.

The first wavelength radiation is split into probe and reference radiation by a second beam-splitter 113. The probe radiation is directed at the target 125 and the reference radiation 116 is directed through a surface 123 that is highly transmissive at the first wavelength range, through a second surface 117 that is partially reflective at the first wavelength range to a third surface 119 that is highly reflective at the first wavelength range.

The highly reflective surface 119 is mounted on an optical path length varying device, which, in the preferred embodiment, said is a length varying piezo device 121. The combination of the highly reflective surface 119 on the length varying piezo device 121 and the partial reflective surface 117 imposes different frequency content on different components of the reference radiation to form composite reference radiation reference radiation which in turn imposes different frequency content on the interferometric signals resulting from combining captured scattered probe radiation with the composite reference radiation as described in patents numbered U.S. Pat. No. 7,526,329 titled Multiple Reference Non-invasive Analysis System and U.S. Pat. No. 7,751,862 titled Frequency Resolved Imaging System, the contents of both of which are incorporated by reference as if fully set forth herein.

The resulting composite interference signals are detected and processed to achieve a scan of the target that consists of a first set of scan segments 141 that are centered around a first wavelength and the separation of the center points of this first set of scan segments, i.e. segment scans associated with the first wavelength is determined by the separation of the reflective surfaces or elements 119 and 117.

A second broadband optical source 109 generates broadband radiation with a wavelength range centered at a second wavelength (different from the first). The second wavelength radiation is focused by a lens 111. The second wavelength radiation is combined with the first wavelength radiation by means of through the beam-splitter 105 that is reflective for radiation at the second wavelength range.

The second wavelength radiation is also split into probe and reference radiation by the second beam-splitter 113. The portion of the probe radiation is also directed at the target 125 and the this portion of the reference radiation 116 is directed through a surface 123 that is partially reflective at the second wavelength range, through a the surface 117 that is highly transmissive at the second wavelength range to the third surface 119 that is also highly reflective at the second wavelength range.

The combination of the highly reflective surface 119 on the length varying piezo device 121 and the partial reflective surface 123 imposes different frequency content on different components of this portion of the reference radiation to form composite reference radiation at the second wavelength range which in turn imposes different frequency content on the interferometric signals resulting from combining captured scattered probe radiation with the composite reference radiation as described in patents numbered U.S. Pat. Nos. 7,526,329 and 7,751,862 which are referenced herein.

The resulting composite interference signals are detected and processed to achieve a scan of the target that consists of a first set of scan segments 143 that are centered around the second wavelength and the separation of the center points of this second set of scan segments, i.e. segment scans associated with the second wavelength is determined by the separation of the reflective surfaces or elements 119 and 123.

In the preferred embodiment the composite interferometric signal that is formed by combining said captured scattered probe radiation associated with the second wavelength range is separated from that associated with the first wavelength range by means of a third beam-splitter 129 that is transmissive (or transparent) at the first wavelength range and reflective at the second wavelength range (or visa versa).

Separating the interferometric signals in this manner enables their detection by detectors 131 and 135 with an appropriate focusing arrangement, for example by means of lenses 127 and 133. It can be appreciated that in some configurations, lenses may not be required. For example, in a very compact miniature configuration with detectors with sufficiently large detection area lenses may not be required.

A control module 139 provides: timing signals (clock, data capture, etc.) to the processing module 137; the modulating drive signal to the piezo device 121; and, typically, drive and temperature control signals to the optical sources 101 and 109.

The detected signals at the two different wavelength ranges can be processed in a coordinated manner because they both share the highly reflective surface 119 and are both modulated by the same length varying piezo device 121, which ensures the first order reference signals of both sets of scan segments corresponds to the same region of the target.

The locations of the regions within the target that the higher order reference signals correspond to are determined by the optical path length separation between the center point of surface 119 and surface 117 in the case of one wavelength range and the center point of surface 119 and surface 123 in the case of the other wavelength range. These optical path length separations can be fixed and therefore known (or determined).

Alternatively the separation of elements in the optical path can be varied so as to vary distance between surfaces, including but not limited to distance between surfaces 119 and 117, and between 119 and 123, so as to change the separation of the midpoints of the scan segments, thus providing additional scanning capability.

For example the two surfaces 117 and 123 could be the surfaces of a single element (as depicted in FIG. 1) mounted on an additional piezo device such that the distance of the surfaces 117 and 123 is dynamically modified. The separation of the center points of the scan segments is likewise dynamically modified, and which consequently results in the scanning of different portions of the target.

Alternatively surfaces 117 and 123 could be on separate elements and be capable of being dynamically varied independently. It can be appreciated that the additional scanning capability leverages the multiple passes of the multiple references in that, for example a 10% change in the separation of surfaces 119 and 123 would cause a 10% change in the span of the set of scan segments. In an ophthalmic application this is useful in in measuring axial lengths of eyes of different length.

Furthermore the optical element between the surfaces 117 and 123 could be selected to for its optical characteristics so as to optimize wave front characteristics of reference radiation so that it best matches wave front characteristics of probe radiation. The surface 123 could be slightly curved (non-flat) to enable focusing the higher order reference radiation of the second wavelength range.

The multiple reflections between surfaces 119 and 123 will cause progressive focusing of the radiation. It can be appreciated that surfaces other than surface 123 could be curved according to the design requirements of the system.

This approach to focusing the higher order reference radiation of the second wavelength range provides additional flexibility which is particularly useful in applications where the target contains a focusing element, such as ophthalmic applications that involve imaging or analysis of the eye, as an eye typically has a lens. In such applications one of the previously mentioned focusing lens may not be required.

In such embodiments that involve the eye as a target the lens of the eye can at least in part be used to focus radiation at the back of the eye. This additional focusing element in the eye can be compensated for in the reference path for the higher order reference radiation of the second wavelength range without significantly affecting the reference radiation of the first wavelength range.

Figure 2:
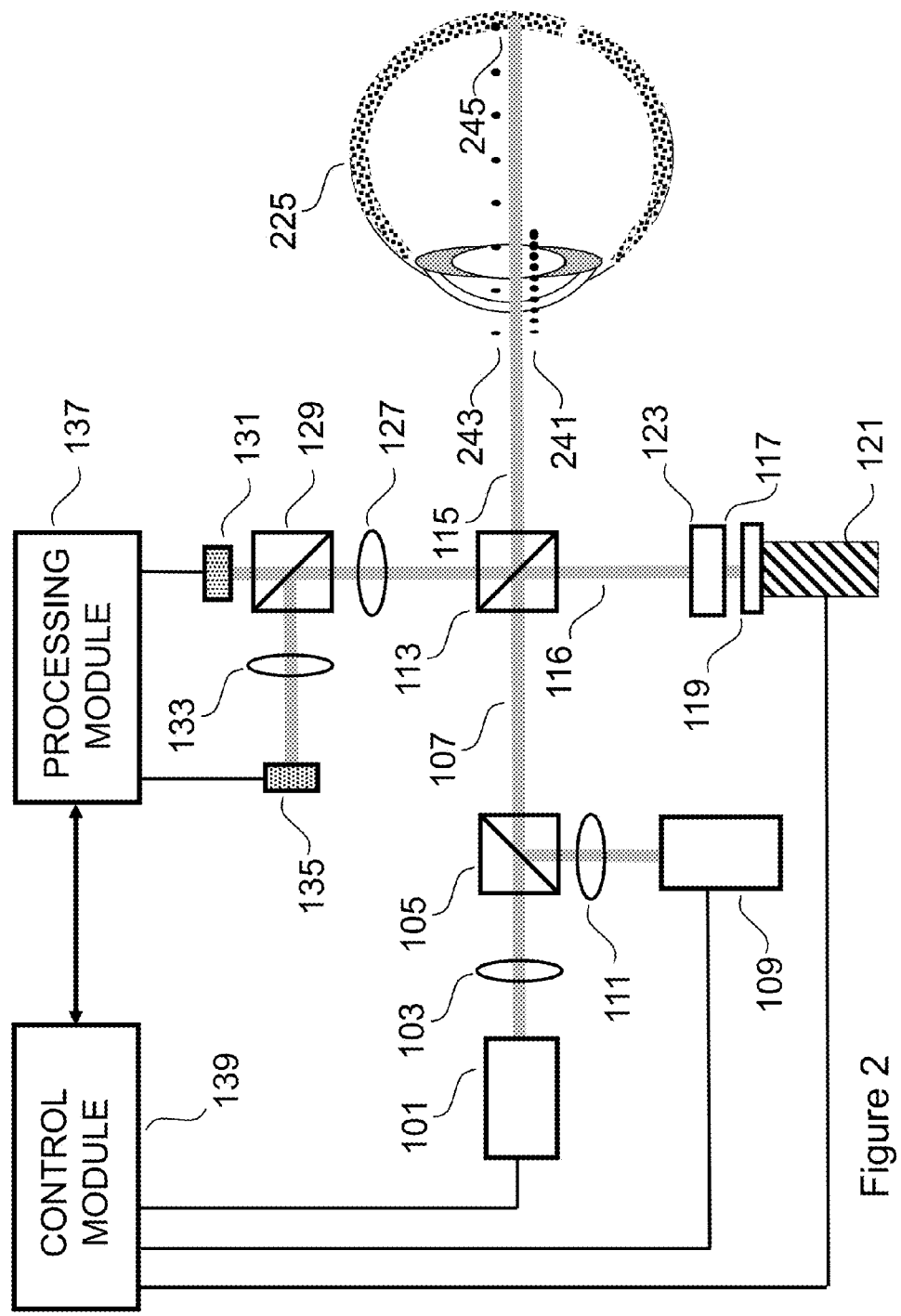
FIG. 2 is a more detailed illustration of a configuration suitable for the application of analyzing or measuring aspects of an eye.

The ophthalmic application is further illustrated in and discussed with respect FIG. 2 which is the same as FIG. 1 except for the target 225 which is an eye. The set of scan segments 241 (close together) determined by reflective surfaces 119 and 117 span the front region of the eye. The set of scan segments 243 (far apart) determined by reflective surfaces 119 and 123 span the full axial length of the eye (one end of which is 245 of FIG. 2).

This enables information about the back of the eye (the retinal area) and information about characteristics of the front of the eye to be acquired such that the distances between the center points of scan segments are known, even when scan segments belong to different sets of scan segments.

Figure 3:
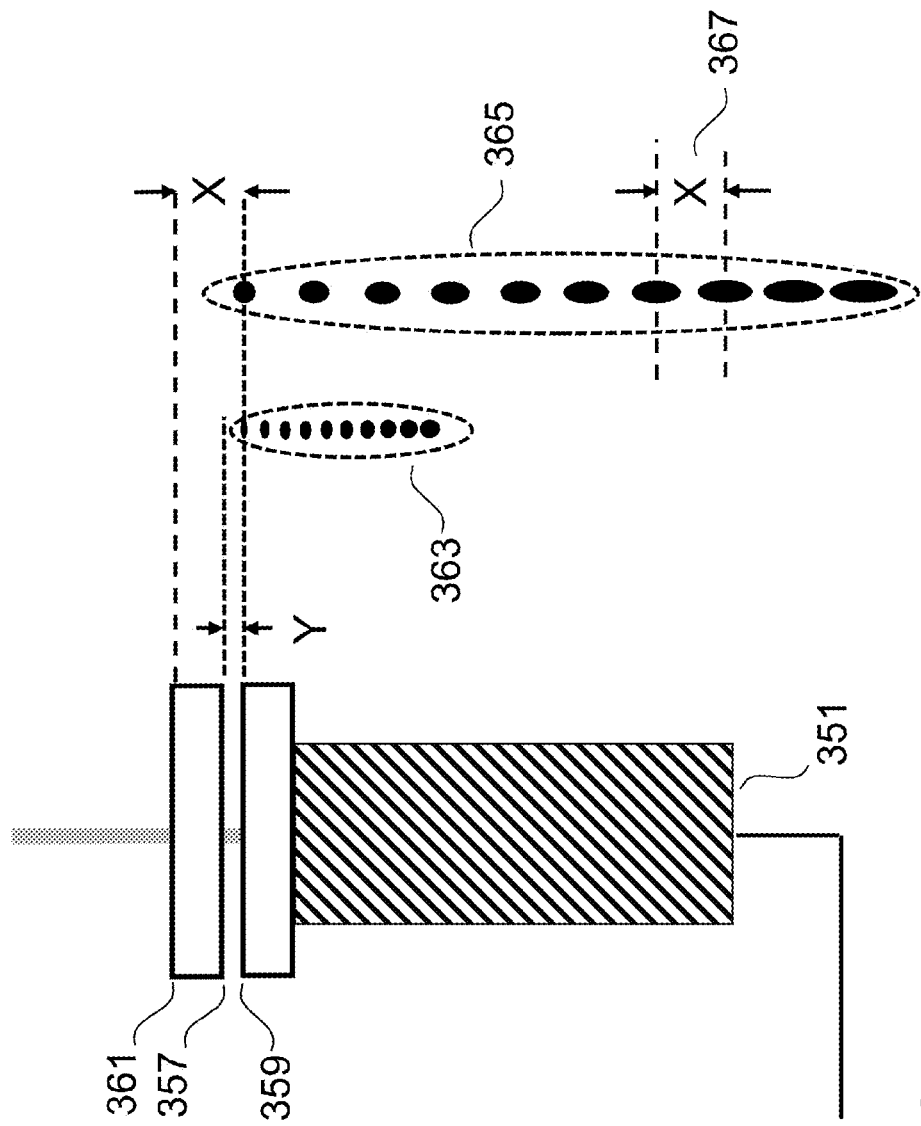
FIG. 3 is a more detailed illustration of one aspect of the configuration depicted in FIG. 2.

The piezo device 121 and reflective surfaces 119, 117 and 123 of FIGS. 1 and 2 and scan segments 241 and 243 of FIG. 2 are depicted in greater detail in FIG. 3. In FIG. 3 the highly reflective surface 359 mounted on piezo device 351 corresponds to the highly reflective surface 119 of FIG. 2. Surfaces 357 and 361 of FIG. 3 correspond to surfaces 117 and 123. The piezo 351 moves the surface 359 in a scan range, and the center point position of the range is the position depicted in FIG. 3.

The magnitude of the separation between surface 357 and the location of surface 359 at the center point of the piezo scan is labeled "Y" and depicted as the distance between two dashed lines (with dashes of the same magnitude). This separation distance "Y" also determines the distance between the center points of the first set of scan segments depicted in the dashed oval 363 (which corresponds to the set of scan segments 241 of FIG. 2).

The magnitude of the separation between surfaces 361 and the location of surface 359 at the center point of the piezo scan is labeled "X" and depicted as the distance between two dashed lines (one of which has larger magnitude dashes than the other). This separation distance "X" also determines the distance between the center points of the second set of scan segments depicted in the dashed oval 365 (which corresponds to the set of scan segments 243 of FIG. 2).

(It should be noted that although the scan segments depicted in oval 365 are larger than those in oval 363, this size difference is simply for ease of illustration.) For example this separation distance "X" if also depicted as the distance 367 between the center points of the $7^{th}$ and $8^{th}$ scan segments. Because the reference signals for first scan segment of both sets 363, 365 of scan segments are generated by the same surface 359, both first scan segments are co-located. In FIG. 2, the first scan segments of 241 and 243 are illustrated as offset, however, in actuality, both first segments occur at the same location with respect to the target.

Furthermore since the distances "X" and "Y" can be determined by virtue of knowing optical distances, the relative locations of the various scan segments in the target likewise can be determined. (It should be noted that the scan segments depicted in the two ovals 363 and 365 of FIG. 3 are shown oriented in the vertical direction for illustrative purposes, as opposed to the actual orientation of the sets of scan segments 241 and 243 of FIG. 2.)

Figure 4:
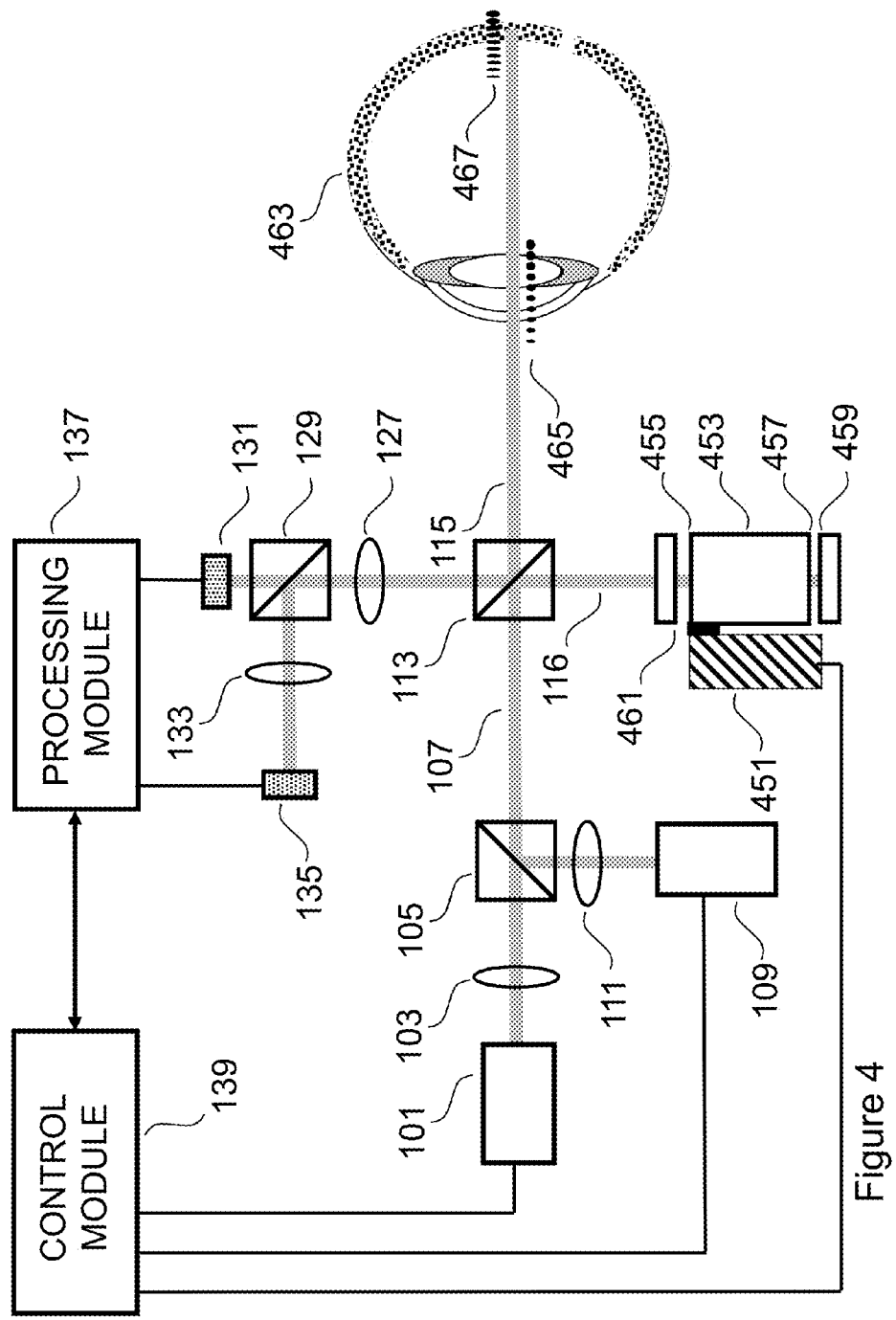
FIG. 4 is an illustration of an alternate embodiment suitable for the application of analyzing or measuring aspects of an eye.

An alternate embodiment is illustrated in FIG. 4 where the optical element 453 with reflective surfaces 457 and 455 is mounted on the piezo device 451. In this embodiment the highly reflective surface 459 and the surface 457, which is partially reflective at a second wavelength range, generates reference signals for the second set of scan segments 467 in the target 463. The surface 455 and the surface 461 generates reference signals for the first set of scan segments 465 in the target 463.

The surface 455 is highly transmissive at the second wavelength range and is highly reflective at a first wavelength range. The surface 461 is highly transmissive at the second wavelength range is partially reflective at the first wavelength range.

In this alternative embodiment the highly reflective surface 459 and the surface 461 may be fixed, or one or both may be adjustable to provide control over one or both of the sets of scan segments.

Figure 5:
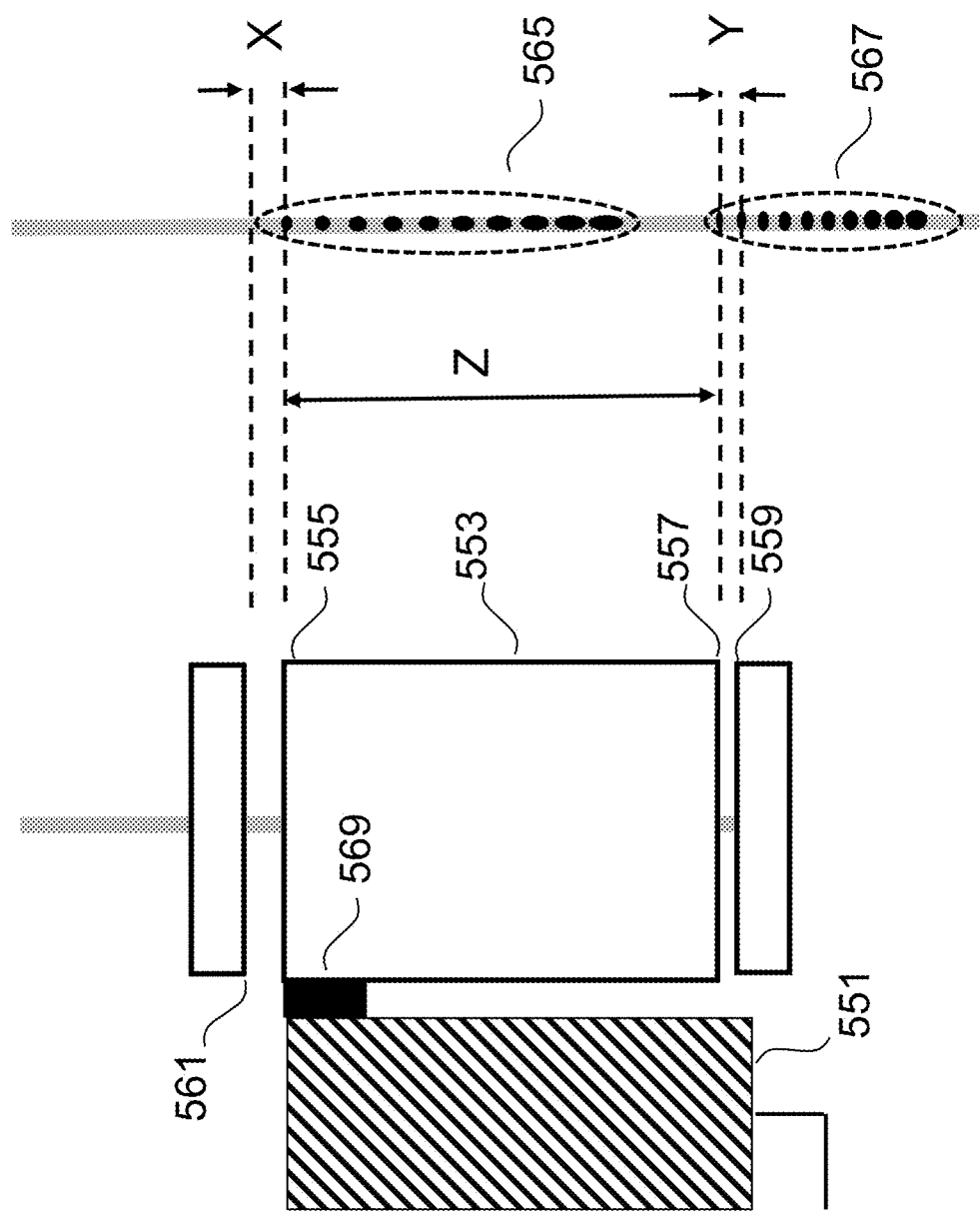
FIG. 5 is a more detailed illustration of one aspect of the configuration depicted in FIG. 4.

Aspects of the alternative embodiment of FIG. 4 are depicted in more detail in FIG. 5. The optical element 553 with reflective surfaces 557 and 557 is mounted on the piezo device 551 by means of a mechanical interface 569. In FIG. 5 the surfaces 555 and 561 generate reference signals for the set of scans depicted in the dashed oval 565. The separation distance indicated by "X" between the surfaces 555 and 561 determines the distance between the center points of the set of scan segments in oval 565.

The location of the first scan segment of this set is determined by the location of the surface 555. The surface 561 is partially reflective at a first wavelength range and highly transmissive at a second wavelength range. The surface 555 is highly reflective at the first wavelength range and highly transmissive at the second wavelength range. The set of scan segments in the oval 565 corresponds to the set of scan segments 465 of FIG. 4.

In FIG. 5 the surfaces 557 and 559 generate reference signals for the set of scans depicted in the dashed oval 567. The separation distance indicated by "Y" between the surfaces 557 and 559 determines the distance between the center points of the set of scan segments in oval 567. The location of the first scan segment of this set is determined by the location of the surface 557. The surface 557 is partially reflective at the second wavelength range. The surface 559 is highly reflective at the second wavelength range.

The distance between the first scan segment of the set of scan segments in oval 565 and the first scan segment of the set of scan segments in oval 567 is determined by the length of the optical element 553, i.e. the distance labeled "Z".

Note all distances in a material are modified by the refractive index of the material in the optical path including element 553 and intervening bio-matter, for example. It should be noted that as depicted the optical element 553 would have an refractive index of 1 (selected for ease of illustration). Further although scan sets 465 and 467 appear on offset parallel lines, in reality both scan sets would be on the same line (i.e. on the probe beam path 115 of FIG. 4 intersecting the target regions).

The magnitude of the separation between surface 557 and the surface 559 at the center point of the piezo scan is labeled "Y" and depicted as the distance between two dashed lines. This separation distance "Y" also determines the distance between the center points of the first set of scan segments depicted in the dashed oval 567 (which corresponds to the set of scan segments 467 of FIG. 4). The magnitude of the separation between surfaces 361 and the location of surface 359 at the center point of the piezo scan is labeled "X" and depicted as the distance between two dashed lines (one of which has larger magnitude dashes than the other).

This separation distance "X" also determines the distance between the center points of the second set of scan segments depicted in the dashed oval 365 (which corresponds to the set of scan segments 243 of FIG. 2). For example this separation distance "X" if also depicted as the distance 367 between the center points of the $7^{th}$ and $8^{th}$ scan segments. Because the reference signals for first scan segment of both sets of scan segments are generated by the same surface 359, both first scan segments are co-located.

Furthermore since the distances "X" and "Y" may be known distances, the relative locations of the various scan segments may be known. Note: For clarity the scan segments depicted in the two ovals 363 and 365 of FIG. 3 are shown oriented in the vertical direction as opposed to the actual orientation of the sets of scan segments 241 and 243 of FIG. 2.

It can be appreciated that the invention provides for accurate distance measurement. In one embodiment of the invention adapted for ophthalmic use, the invention enables accurate determination of distances between elements in the eye. Other bio-metric uses can be readily conceived within the scope of the present invention.

There are many variations of the described embodiment possible. For example, optical path length varying devices other than piezo devices, such as voice coils, could be used. There can be many variations of collimating and focusing devices, for example holographic elements can be used to address focusing, wave front distortion aspects.

For example, the element between surfaces 123 and 117 of FIGS. 1 and 2 or the element between surfaces 455 and 457 of FIG. 4 could be an electro-static controllable liquid or gel or similarly behaving fluid which could contain additives to match distortion in the target and whose shape could be adjusted electrically to compensate for wave front distortion and to match focusing aspects. In particular these aspects can be dynamically adjusted within the time frame of a scan.

As can be appreciated by those with average skill in the relevant art, such an electro-static controllable element may be used in a conventional OCT systems (Fourier or time domain) or a multiple reference OCT system, and it is not limited to the dual wavelength system as described herein. For example such an electro-static controllable element may be installed in the optical path of the probe beam or the reference beam or both to dynamically compensate for wave front distortion or focusing aspects of the target or the scanning mechanism.

For example, in the case of a conventional time domain OCT system focusing of the probe and reference beam could be dynamically modified by means of at least one the electro-static controllable element substantially synchronously with the time domain scanning Wave front distortion could be similarly dynamically synchronously compensated and speckle reduced. For example, additional dynamic angular scanning of the probe beam could be performed by means of an electro-static controllable element.

Alternatively focusing and wave front compensation of the probe and reference beam could be dynamically modified by means of at least one the electro-static controllable element at a lower frequency than the OCT scanning frequency to optimize scanning of different regions of the target at different times. This would be useful in multiple reference time domain OCT scanning where information is acquired from multiple depths simultaneously and Fourier domain OCT which is typically high speed scanning if swept source and also where information is acquired from multiple depths simultaneously.

Alternatively or in addition, the element between surfaces 123 and 117 of FIG. 2 could be selected to provide dispersion compensation for dispersion of the material of the target. People with skill in the art will select a material with appropriate chromatic dispersion so as to generate dispersion that approximately matches dispersion in the target. It can be appreciated that the deeper or higher order scan segments of the set of scan 243 experience greater dispersion compensation due the additional passes through the element between surfaces 123 and 117 with increasing order.

First and second wavelengths used in broadband radiation can be selected to suit particular applications, for example in the ophthalmic application wavelengths of 800 nm and 1050 nm could be used.

Other examples will be apparent to persons skilled in the art. The scope of this invention should be determined with reference to the specification, the drawings and the appended claims, along with the full scope of equivalents as applied thereto.

What is claimed is:

1. An apparatus for scanning a target, said apparatus comprising:

a first broadband optical source, said first broadband optical source generating first broadband radiation with a first wavelength range centered at a first wavelength, hereafter referred to as first wavelength radiation;

a first beamsplitter, said first beamsplitter transmissive for radiation at said first wavelength range;

a second beamsplitter, said second beamsplitter splitting said first wavelength radiation into first probe radiation and first reference radiation, said first probe radiation directed to said first target region;

and said first reference radiation directed in a first reference optical pathway;

a first surface in said reference optical pathway, said first surface highly transmissive at said first wavelength range;

a second surface parallel to and at some distance from said first surface, said second surface partially reflective at said first wavelength range;

a third surface, parallel to and at some distance from said second surface, said third surface highly reflective at said first wavelength range;

an optical path length varying device, upon which said optical path length varying device said third surface is mounted;

wherein the combination of said third surface, highly reflective for first wavelength radiation, mounted on said optical path varying device, and said second surface, partially reflective of said first wavelength radiation, said combination imposes different frequency content on different components of said first wavelength reference radiation so as to form a first composite reference radiation, said first composite reference radiation in turn imposes different frequency content on the interferometric signals resulting from combining captured scattered first probe radiation with said first composite reference radiation, and produces a first set of resulting composite interference signals;

a third beamsplitter, said third beamsplitter transmissive of first wavelength radiation in said first reference optical path;

a first detector, said first detector detecting said first set of resulting composite interference signals;

a processing module, said processing module including a microprocessor and coupled to said rust detector and a control module, where said processing module outputs a first scan of said target, said first scan consisting of a first set of scan segments that are centered around a first wavelength and where the separation of the center points of said first set of scan segments, is determined by the distance between said second surface and said third surface;

a second broadband optical source, said second broadband optical source generating broadband radiation with a wavelength range centered at a second wavelength, said second wavelength being different from said first wavelength, hereafter referred to as said second wavelength radiation;

said first beam splitter, said first beam splitter reflective for radiation at said second wavelength range;

said second beamsplitter, said second beamsplitter splitting said second wavelength radiation into second probe radiation and second reference radiation, said second probe radiation directed to said second target region, and said second reference radiation directed in a second reference optical pathway said first surface in said second reference optical pathway, said first surface partially reflective of said second wavelength range, said second surface parallel to and at some distance from said first surface, said second surface highly transmissive at said second wavelength range;

said third surface, parallel to and at some distance from said second surface, said third surface highly reflective at said second wavelength range;

said optical path length varying device, upon which said optical path length varying device said third surface is mounted, wherein the combination of said third surface, highly reflective for second wavelength radiation, mounted on said optical path varying device, and said first surface, partially reflective of said second wavelength radiation, where said combination imposes different frequency content on different components of said second wavelength reference radiation so as to form a second composite reference radiation, and said second composite reference radiation in turn imposes different frequency content on the interferometric signals resulting from combining captured scattered second probe radiation with said second composite reference radiation, and produces a second set of resulting composite interference signals;

said third beamsplitter, said third beamsplitter transmissive of second wavelength radiation;

a second detector, said second detector detecting said second set of resulting composite interference signals;

said processing module, said processing module coupled to said second detector and said control module, where said processing module outputs a second scan of said target, said second scan consisting of a second set of scan segments that are centered around a second wavelength and where the separation of the center points of said second set of scan segments, is determined by the distance between said first surface and said third surface; and display device, whereby said first scan and said second scan are displayed in accurate relation to said first and second regions of said target.

2. The apparatus as in claim 1 wherein the separation of elements in the reference optical path can be varied so as to vary distance between said first, second and third surfaces, changes the separation of the center points of resulting scan segments, thus providing additional scanning capability.

3. The apparatus as in claim 2 wherein said distances between said first, second and third surfaces are dynamically modified, such that separation of the center points of said resulting scan segments are likewise dynamically modified, and thereby provides for selectably governing regions of target depicted in scan output.

4. The apparatus as in claim 3 wherein said distances between said first, second and third surfaces may be dynamically varied independently.

5. The apparatus as in claim 1, wherein said first and second wavelengths are selected to optimize ophthalmic applications, enabling scanning of the axial length of an ophthalmic target.

6. The apparatus as in claim 1 wherein the length of a reference optical path can be varied so as to vary distance between at least some of said first, second and third surfaces, changes the separation of the center points of resulting scan segments, thus providing additional scanning capability.

7. The apparatus as in claim 6 wherein said distances between said first, second and third surfaces are dynamically modified, such that separation of the center points of said resulting scan segments are likewise dynamically modified, and thereby provides for selectably governing regions of target depicted in scan output.

8. The apparatus as in claim 6 wherein said distances between said first, second and third surfaces may be dynamically varied independently.

9. The apparatus as in claim 1 wherein said first and second wavelengths are selected to optimize ophthalmic applications, enabling measurement of the distance between surfaces of an ophthalmic target.

10. The apparatus as in claim 1 wherein said first and second wavelengths are selected to optimize ophthalmic applications, enabling measurement of the axial length of an ophthalmic target.

11. The apparatus as in claim 1, further including material between at least two of said first, second and third surfaces, said material selected to compensate for wavefront distortion.

12. The apparatus as in claim 1, further including material between at least two of said first, second and third surfaces, said material selected to compensate for dispersion.

13. The apparatus as in claim 1, wherein one of said first, second and third surfaces has at least one curve, enabling compensation for focusing elements present in said target.

14. The apparatus as in claim 1, wherein modification of the length of the reference optical path is accomplished by any one or more of the following:
   one or more piezos,
   electromechanical voice coil,
   electrostatic gel.

15. The apparatus as in claim 13, wherein at least one of said first, second or third surface is the surface of an electrostatic gel.

* * * * *